United States Patent [19]
Heff

[11] Patent Number: 5,807,235
[45] Date of Patent: Sep. 15, 1998

[54] SURGICAL TOOL HOLDING AND POSITIONING DEVICE

[76] Inventor: Allan Heff, 17 Shanley St. #4, Brighton, Mass. 02135

[21] Appl. No.: 709,335

[22] Filed: Sep. 27, 1996

[51] Int. Cl.⁶ .................................................. A61B 1/00
[52] U.S. Cl. .......................... 600/102; 600/104; 600/114
[58] Field of Search ..................... 600/102, 114, 600/115, 227, 104, 123; 604/264, 93, 280, 281; 606/108

[56] References Cited

U.S. PATENT DOCUMENTS

| | | |
|---|---|---|
| 254,457 | 3/1882 | Caps . |
| 4,686,981 | 8/1987 | Forintos ............................. 128/303 |
| 4,688,554 | 8/1987 | Habib ................................ 600/114 |
| 4,763,669 | 8/1988 | Jaeger ............................... 128/751 |
| 4,880,015 | 11/1989 | Nierman ............................ 128/751 |
| 5,195,506 | 3/1993 | Hulfish ............................. 128/20 |
| 5,275,608 | 1/1994 | Forman et al. ..................... 606/170 |
| 5,284,128 | 2/1994 | Hart ................................... 128/4 |
| 5,325,845 | 7/1994 | Adair ................................ 600/114 |
| 5,330,502 | 7/1994 | Hassler et al. .................... 606/205 |
| 5,350,391 | 9/1994 | Iacovelli .......................... 606/170 |
| 5,354,311 | 10/1994 | Kambin et al. .................... 606/205 |
| 5,374,277 | 12/1994 | Hassler ............................. 606/207 |
| 5,383,888 | 1/1995 | Zvenyatsky et al. .............. 606/206 |
| 5,386,818 | 2/1995 | Schneebaum et al. ............ 600/104 |
| 5,390,664 | 2/1995 | Redmond et al. ................. 128/20 |
| 5,417,203 | 5/1995 | Tovey et al. ...................... 128/4 |
| 5,454,827 | 10/1995 | Aust et al. ........................ 606/170 |
| 5,456,695 | 10/1995 | Herve Dallemagne ............ 606/207 |
| 5,474,057 | 12/1995 | Makower et al. ................. 600/214 |
| 5,514,157 | 5/1996 | Nicholas et al. .................. 606/206 |

FOREIGN PATENT DOCUMENTS 43 00 307 A1  7/1994  Germany .................. A61B 17/30

*Primary Examiner*—Beverly M. Flanagan
*Attorney, Agent, or Firm*—George W. Neuner

[57] ABSTRACT

A tool holding and positioning device for remote operation through a narrow opening is described. The tool holding and positioning device has a proximal end, an elongated first tubular member extending from the proximal end, and a distal end. A second tubular member is attached to the first tubular member for rotation about a fixed point adjacent the distal end thereof to position the second tubular member in a particular angle with respect to the longitudinal axis of the first tubular member. A first rod or cable is connected between the proximal end and the second tubular member for controlling its angular position with respect to the longitudinal axis. A second rod or cable is extended from the proximal end through the first and second tubular members to support and position tool means at a variable distance from the fixed point. The tool means are operatively connected to the second rod or cable and are controlled by control means operated from the proximal end.

18 Claims, 2 Drawing Sheets

SURGICAL TOOL HOLDING AND POSITIONING DEVICE

FIELD OF THE INVENTION

The present invention relates to devices used in surgery, particularly neurosurgery, for example, to enable the holding and positioning of the surgical tools needed for minimally invasive neurosurgery through a narrow aperture in the skull and brain.

BACKGROUND OF THE INVENTION

The treatment of brain tumors is different from the treatment of tumors in other parts of the body. The brain prevents many therapeutic drugs from entering due to the blood brain barrier. Surgery can be the treatment of choice for accessible brain tumors. Accessible tumors are those which can be surgically removed without causing severe neurological damage. For example, tumors located in gray matter or deep within the brain may be inaccessible.

If the brain tumor is accessible and the patient's general health is good, resection can be effective. Removal of the entire tumor is desirable. The most commonly performed surgery for removal of a brain tumor is a craniotomy where the neurosurgeon makes an incision into the scalp and removes a piece of bone to expose the area of brain over the tumor location and to remove the tumor.

The neurosurgeon has a wide choice of tools to use in removing brain tumors. Commonly used surgical tools include a laser, an ultrasonic transducer, a bipolar or monopolar cautery device, an irrigator, an aspirator, and the like. Passive tools such as a operating microscope or fiber optics (flexible endoscope) for visualization and illumination are also used. Usually, such surgical tools are readily available at major medical institutions. The tools used for a particular surgical removal depend on the type of tumor and its location.

Thus, typically, the removal of a brain tumor requires boring a hole through the skull, dura (the membrane surrounding the brain), and brain tissue in order to reach the tumor. The brain tissue in the path of this hole is destroyed. This hole must be wide enough (often two inches in diameter) to allow a straight, rod-like tool to reach from outside the brain to all points of the tumor. The large bore hole has several disadvantages. First, because of the pressure imbalance between the inside and outside of the brain, the large hole in the dura causes shifts in the brain tissue and the location of structures within the brain. Because of this, at the time of surgery, the brain structures generally have shifted position from the locations determined by imaging used for the planning the surgery. However, the shifting does not occur for small holes in the dura. Second, large portions of the brain must be destroyed to create the passage bored through the brain tissue in order to reach the tumor. Third, it is often difficult to find an acceptable path to the tumor which does not destroy critical areas of brain function.

For these reasons it would therefore be useful to have a narrow diameter surgical tool which can reach through the brain tissue to some central point located relatively deep in the brain. From this central point the tool would, without affecting the position of the tool through the brain to the central point, pivot in any direction and elongate in that direction in order to reach all points inside a spherical volume (which has a radius much larger than the diameter of the tool, but small compared to the length of the tool) centered at that point. This sphere should correspond to the size of a tumor.

Surgical devices have been proposed for entrance into a body cavity through a small hole and remote manipulation of tissue. For example, U.S. Pat. No. 5,350,391 discloses a laparoscopic surgical instrument that comprises an elongated hollow shaft having at one end a pair of scissors and at the other end a pair of handles to control the scissors. The orientation of the scissor blades relative to the shaft can be changed to cut or grasp curved tissues lying in a plurality of planes.

U.S. Pat. No. 5,275,608 discloses a surgical tool having an elongated rigid member, at one end of which is mounted a head for movement in at least one plane through an angle with respect to the axis of the rigid member. An operable control member is mounted on the opposite end of the rigid member.

U.S. Pat. No. 5,330,502 discloses an endoscopic instrument such as a dissector, scissor or grasper in which there is provided a shaft which defines a longitudinal axis. The shaft can rotate about the handle portion of the instrument. A mechanism provides for articulation of the end effector by causing angulation of the end effector with respect to the shaft.

U.S. Pat. No. 5,383,888 discloses a surgical instrument for use in endoscopic or laparoscopic surgery. The instrument includes a handle portion and an endoscopic portion. The endoscopic portion has an elongated tubular section, at the proximal end of which is a handle portion, and an articulating section pivotally connected at the distal end. Tool means depend from the articulating section and a linkage mechanism pivots the articulating section relative to the longitudinal axis within a 90° sector of rotation.

U.S. Pat. No. 5,454,827 discloses an arthroscopic or endoscopic surgical instrument that has a manually engageable handle, a rigid stem section connected to the handle, and tissue engaging means comprising first and second tissue engaging members. An articulated shaft is connected between the stem section and the tissue engaging means and supports the tissue engaging means for movement between a plurality of orientations relative to the stem section.

U.S. Pat. No. 5,354,311 discloses forceps having forceps jaws operated by a handle with a cable connected between the forceps jaws and a manual actuator such that the forceps jaws are swung to a desired position when the actuator is operated.

U.S. Pat. No. 5,417,203 discloses an endoscopic instrument which includes a handle portion and an endoscopic portion. The endoscopic portion has a fixed inner tubular section which depends from the handle and an outer tubular section mounted for coaxial reciprocating movement with respect to the inner tubular section. A resilient articulating member is attached to the fixed inner tubular section and is movable in response to reciprocating movements of the outer tubular section between a first unstressed position and a second stressed position. Tool means are operatively connected to the distal end of the resilient articulating member for performing surgical tasks.

Thus, several surgical devices exist which enter the body through a narrow aperture and at some internal point have a distal portion that can pivot about a hollow shaft member at that internal point. However, the length of the distal portion is fixed in such devices. Thus, the use of these devices in surgery is limited when the device is fixed relative to a body cavity. Thus, it can be appreciated that improved surgical devices are required, particularly for neurosurgery.

SUMMARY OF THE INVENTION

The present invention provides a tool holding and positioning device for remote operation through a narrow opening and permits the operator to freely change the distance of a distal operating tool from a pivotable part of the device while maintaining the device in a fixed relationship with the opening.

A tool holding and positioning device, in accord with the present invention, comprises an elongated first tubular member having a longitudinal axis extending from a proximal end to a distal end thereof. A second tubular member is attached to the first tubular member for rotation about a fixed point adjacent the distal end thereof to position the second tubular member in a particular angle with respect to the longitudinal axis of the first tubular member. A first rod or cable is extending from the proximal end and connected to the second tubular member for controlling its angular position with respect to the longitudinal axis. A second rod or cable is extended from the proximal end through the first and second tubular members to support and position tool means at a variable distance from the fixed point. Thus, the second rod is movable in a linear manner to position the tool means supported at the distal end of the second rod. The tool means are operatively connected to the second rod or cable and are controlled by control means operated from the proximal end.

In operation, a surgical device in accord with the present invention is used by inserting the distal end of the elongated first tubular member and the second tubular member through a small opening so that the distal end is positioned in a desired position in a body cavity. The device preferably is fixed rotatably in this position relative to the opening and body cavity. In other words, the device is fixed along the direction of its longitudinal axis and with respect to the opening, but can be rotated about the longitudinal axis. Typically, a portion of the elongated first tubular member is held by a clamp or other device. If the fixation is not critical and movement of the distal end within the cavity can be tolerated, the device can be held manually.

Non-surgical uses for this device also exist where it is desirable to manipulate objects in a difficult to reach location through a narrow access aperture.

DETAILED DESCRIPTION OF THE INVENTION WITH REFERENCE TO THE PREFERRED EMBODIMENTS

Figure 1:
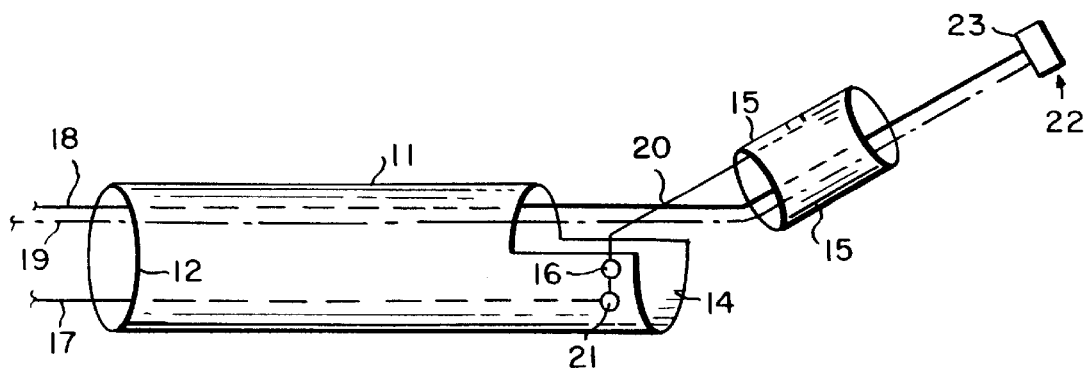
FIG. 1 is an isometric view illustrating a neurosurgical tool holding and positioning device in accord with one embodiment of the present invention.

As illustrated in FIG. 1, a surgical tool holding and positioning device 10, in accord with one embodiment of the present invention, comprises an elongated first tubular member 11 having a proximal end 12 and a distal end 14. A second tubular member 15 is attached to the first tubular member for rotation about a fixed point 16 adjacent the distal end thereof to position the second tubular member in a particular angle with respect to the longitudinal axis of the first tubular member. A first rod 17 or cable is connected between the proximal end and the second tubular member for controlling its angular position with respect to the longitudinal axis. A second rod 18 or cable is extended from the proximal end through the first and second tubular members to support and position tool means at a variable distance from the fixed point. The tool means are operatively connected to the second rod or cable and are controlled by control means (e.g., tool leads 19) operated from the proximal end. The second rod or cable can be moved linearly through the first and second tubular members to position the tool means at a desired variable distance from the fixed point.

The first tubular member 11 has a length so that it can be inserted into a body and easily reach the region of interest. The distal end of the first tubular member is preferably located at the center of the region of interest. The first tubular member has a diameter to be inserted through a relatively narrow aperture in the body but of sufficient size through which can be inserted rods or cables to angularly position the second tubular member 15 and operate the surgical tools held at the distal end of the second tubular member.

The first tubular member can be made of any material typically used for surgical tools or body implants. Such materials include stainless steel, various plastics, and the like.

The second tubular member 15 is generally smaller in length than the first tubular member and can be of smaller diameter. The second tubular member is positioned at the distal end of the first tubular member to which it is rotationally connected at pivot point 16. The second tubular member can be pivoted or rotated with respect to the longitudinal axis of the first tubular member by use of angular position control rod 17 which is connected to the second tubular member through distal rod 20, on which the second tubular member is mounted for angular rotation about pivot point 16. The angular position control rod 17 and distal rod 20 are coupled at 21 by a suitable coupling (not shown). By use of the angular position control rod 17, the longitudinal axis second tubular member can positioned relative to the longitudinal axis of the first tubular member in any angle from about 0° to about 150°, depending on the geometry of the distal end of the first tubular member. The second tubular member, angular position control rod and distal rod can also be made of any known material useful for surgical tools or body implants.

A second rod 18 or cable, i.e., the elongating rod or cable, is used to position the surgical tool linearly relative to the pivot point 16. The rod or cable is preferably made of a moderately stiff material and extends through the first tubular member and second tubular member to a tool holding means, at which a particular surgical tool is attached. The elongating rod moves in a linear manner, but is flexible enough to bend in accord with the angular position of the second tubular member relative to the first tubular member. Its linear motion is controlled by the operator to position the surgical tool within the patient. The degree of bending of the elongating rod 18 is controlled by the operator via the angular position control rod 17.

Thus, the surgical tool held at the effecting end of the surgical tool holding and positioning device 10 can be moved in a straight line in a direction that differs from the direction with which the device 10 passes through the small aperture in the patient. A surgical tool held at the effecting end of the device 10 can access all points in a large volume accessible only through a small aperture even though most of those points would be inaccessible to a surgical tool that can be moved only in a straight line from the aperture.

It can be appreciated that the angle between the longitudinal axis of the first tubular member and the longitudinal axis of the second tubular member is controlled by the position of the angular position control rod 17 or cable passing through the first tubular member. Various known mechanical devices can be used to control the position of the angular position control rod or cable. Two such devices are illustrated in FIGS. 2 and 3.

Figure 2:
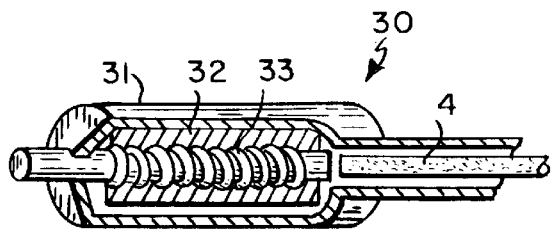
FIG. 2 is an isometric view of a micrometer type retracting mechanism useful for positioning surgical tools using a surgical tool holding and positioning device in accord with an embodiment of the present invention.

In FIG. 2 is illustrated a conventional micrometer type mechanism for precision positioning of the angular position control rod. The micrometer mechanism 30 has a knob 31 at the proximal end. When the knob is turned, it turns a screw 33 which rotates in a screw block 32. Either the threaded portion of the screw or the screw block is fixed to prevent longitudinal movement. The component that is not fixed is connected to the angular position control rod so that turning of the knob and thus the threaded portion in the screw block causes linear longitudinal movement of the rod to adjust the angular position of the second tubular member.

Figure 3:
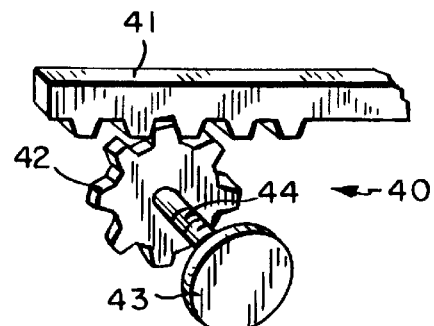
FIG. 3 is an isometric view of a rack and pinion type retracting mechanism useful for positioning surgical tools using a surgical tool holding and positioning device in accord with an embodiment of the present invention.

FIG. 3 illustrates an alternative rack and pinion mechanism for positioning of the angular position control rod. The rack and pinion mechanism has rack 41 which is engaged by a pinion 42. The pinion is rotated by use of a knob 43 to move the rack, which is connected to the control rod and moves the rod linearly. Optionally, the pinion is connected to the knob by a threaded rod 44, which can cooperate with a screw block (not shown) to obtain fine control of the movement of the rack and pinion.

Figure 4:
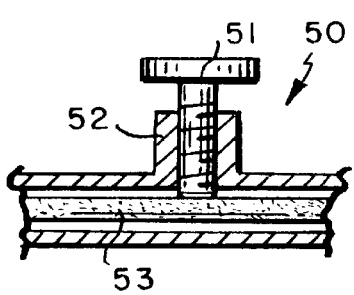
FIG. 4 is a side elevational view, partly in cross-section, illustrating a locking mechanism for holding a surgical tool in a fixed position in a surgical tool holding and positioning device in accord with an embodiment of the present invention.

Preferably, a locking device as illustrated in FIG. 4 is included to lock the position and prevent movement of the angular position control rod. The locking device 50 has a screw 51 that is turned in a screw block 52 to engage the rod 53. When the screw engages the rod, movement of the rod is prevented.

The position control mechanism and locking device preferably is used with both the angular position control rod 17 and the elongating rod 18.

The angular position control rod 17 is connected to the distal rod 20 by a coupling (not shown). The distal rod 20 is attached to the second tubular member 15 and connects it to the first tubular member by the coupling to the angular position control rod. The distal rod is securely attached to the second tubular member and can be an integral part thereof. The distal rod preferably is bent in an L-shape, or approximate L-shape, so that it can be attached to the wall of the second tubular member and connected through the coupling to the angular position control rod in a manner to permit the second tubular member to be positioned along the same longitudinal axis as the first tubular member. The angle of the short arm relative to the long arm of the distal rod is preferably from about 90° to about 135°.

The angular position control rod 17 and the distal rod 20 rotate freely with respect to each other at coupling 21. The distal rod is connected to the first tubular member at the pivot coupling 16, which is fixedly located near the distal end of the first tubular member and around which the distal rod pivots to adjust the angle of the second tubular member relative to the longitudinal axis of the first tubular member. The first tubular member can be cut open at the distal end to allow greater freedom of motion for the distal rod.

The distance between the pivot point 16 and the effecting end 22 of the device 10 is controlled by the elongating rod 18. This rod is made of a moderately stiff material that is (i) sufficiently flexible as to bend easily near the pivot and (ii) sufficiently stiff that it does not buckle within the first tubular member and the portion of the elongating rod that extends beyond the distal tube remains straight. Thus, the elongating rod must be stiff compared to the medium through which a tool at the effecting end of the device is moved.

By way of example, a material for an elongating rod mechanically suitable for use in brain tissue is a 0.05 inch diameter brass rod. The elongating rod can be made of any material of suitable stiffness and strength, including metals and plastics. The angular position control rod and distal rod can be made of similar materials. However, no flexibility is required for this rod. The distal rod must be rigid enough to move the second tubular member and hold it in the desired angular position.

At the distal end 22 of the elongating rod 18 preferably is attached a tool holding member or tool holder platform 23. This is the effecting end of the device 10. The tool holder platform permits different surgical tools to be mounted and operated at the end of the tool positioning and holding device of the present invention. The surgical tools are operated by tool leads 19, which are inserted through the first and second tubular members and are manipulated at the proximal end of the first tubular member. The tool holder platform is moved radially with respect to the pivot point 16 by the elongating rod 18.

Various surgical tools can be mounted on the tool holding platform and operated by tool leads. Examples of surgical tools that can be mounted on the tool holding platform include an a laser, an ultrasonic transducer, a bipolar or monopolar cautery device, an irrigator, an aspirator, and the like. Also, passive tools such as an operating microscope or fiber optics (flexible endoscope) for visualization and illumination can be mounted.

The tool holding and positioning device of the present invention is useful in a variety of surgical procedures in which it is desired to create a minimum opening or aperture into the patient. In brain surgery, the surgical tool holding and positioning device of the present invention is inserted through an opening drilled into the skull so that the position of the distal end within the cavity is at the center of a sphere in which the surgical tool is desired to be operated. The diameter of the elongated first tubular member is much smaller than the diameter of the sphere and the length of the first tubular member is larger than the radius of the sphere. The second tubular member at the distal end of the device extends radially outward from the center of the sphere, i.e., the fixed point around which the second tubular member pivots. Various surgical tools can be supported at the distal end of the second tubular member. Without changing the location of the first tubular member within the cavity, the surgeon can move the surgical tool through all points in the sphere. The position of the points within the sphere can be described by three coordinates: the distance from the point to the center of the sphere, the azimuthal angle between the longitudinal axis of the first tubular member and a line from the center of the sphere to the point, and the rotational angle around the longitudinal axis of the first tubular member. The distance between the surgical tool and the center of the sphere is controlled by the elongating rod. The azimuthal angle is controlled by the angular position control rod. The tool can be rotated about the longitudinal axis of the first tubular member by rotating the tubular member about its longitudinal axis. Thus, access to a spherical region is obtained.

Figure 5:
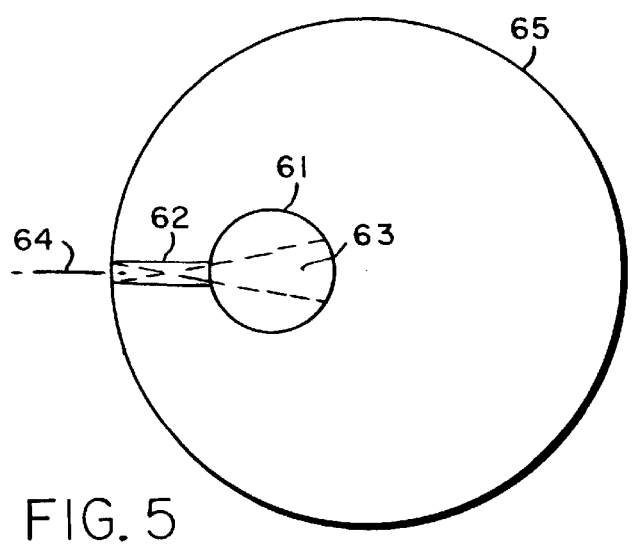
FIG. 5 is a schematic illustrating the region accessible through a narrow bore by prior art methods versus the region accessible through a narrow bore using a surgical tool holding and positioning device in accord with the present invention.

FIG. 5 illustrates a planar view of a tumor in a circular region 61 within a skull 65. A narrow bore hole 62 is shown for insertion of surgical tools. Conventional methods of surgery permit access only to the shaded region 63 within the circle 61. However, the surgical tool positioning and holding device of the present invention permit access to the entire circular region 61. Rotation of the device provides access to a spherical region defined by rotating the circular region about the longitudinal axis 64 through the bore hole 62.

In a preferred embodiment of the present invention, the surgical device is adapted and arranged for the resection (removal) of tumors in the brain. The surgical device of the present invention can also be adapted for the application of aneurysm clips to vascular lesions. It can also be used for surgical procedures in other parts of the body, especially in the thorax, the liver, the retroperitoneal and perispinal areas. An example in the perispinal area is the excision of a herniated disk.

Figure 6:
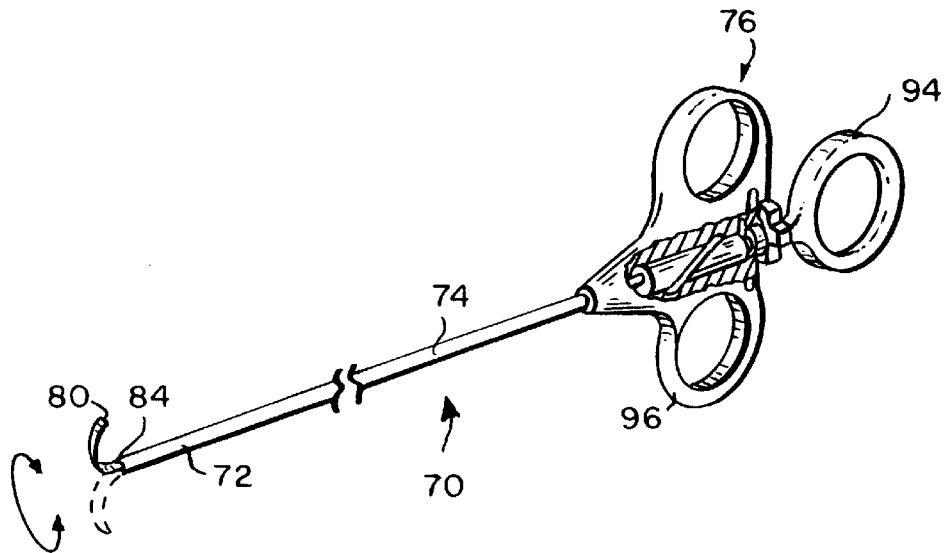
FIG. 6 illustrates a retractor device as one embodiment of a tool that can be positioned and held by use of the tool holding and positioning device of the present invention.
Figure 7:
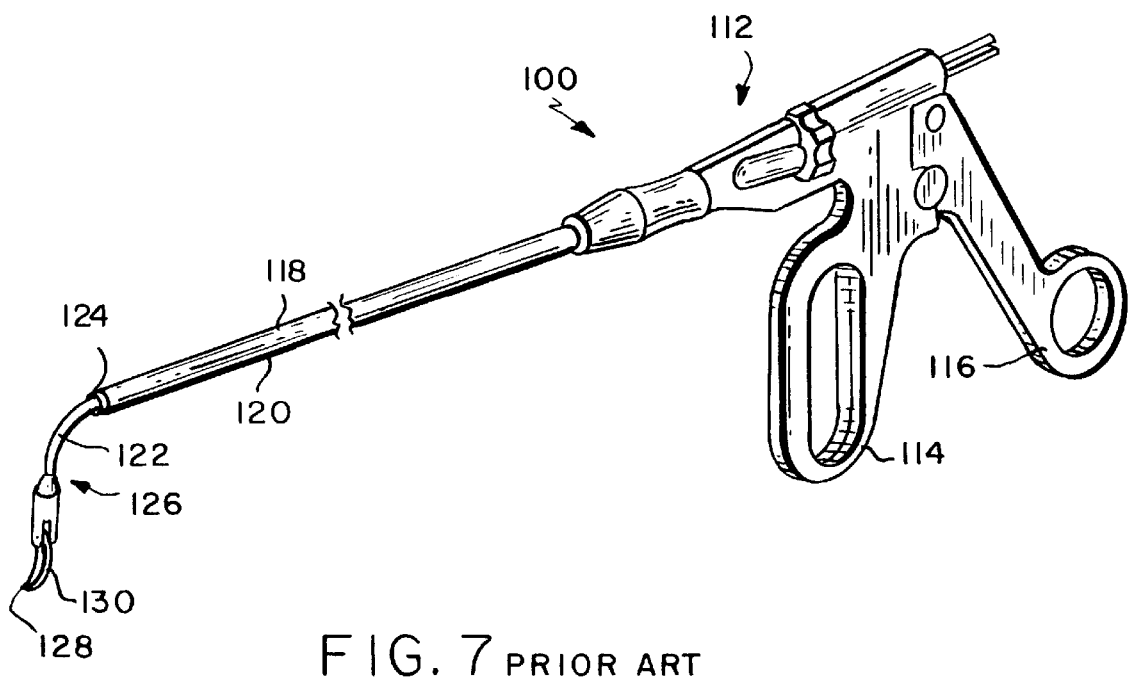
FIG. 7 illustrates an endoscopic instrument as another embodiment of a tool that can be positioned and held by use of the tool holding and positioning device of the present invention.

FIGS. 6 and 7 are examples of surgical tools that can be mounted on the tool holding platform and operated by tool leads through the tubular members of the surgical tool positioning and holding device of the present invention. FIG. 6 shows a percutaneous surgical retractor 70 having a retractor blade assembly 72, elongated tubular housing means 74, and a handle assembly 76. The distal end of the elongated tubular housing means is attached by suitable clamping means (not shown) to the tool holding platform of the device of the present invention. Thus, the retractor blade 80 can be positioned by movement of the tool holding platform. The elongated tubular housing means is flexible and contains tool leads for operation of the retractor blade by means of the handle assembly 76. The retractor blade is displayed or retracted by pushing or pulling ring 94 relative to grip member 96. Rotation of ring 94 rotates the retractor blade 80 for cutting tissue. The retractor is described in more detail in U.S. Pat. No. 5,512,037, which is hereby incorporated by reference.

FIG. 7 shows another surgical instrument for use in minimal invasive surgical procedures, which can be used with the surgical tool positioning and holding device of the present invention. The surgical instrument 100 comprises a handle portion 112 which includes a fixed handle 114 and a pivoting handle 116. An endoscopic portion 118 of the instrument is attached to the handle portion 112 and includes an elongated cylindrical portion 120 and an articulating member 122. The articulating member 122 is connected to the distal end 124 of the cylindrical portion 120 and is preferably formed from a resilient material. A tool head 126 depends from the articulating member 122 and includes cooperating jaws 128, 130. The cooperating jaws 128, 130 can be configured as graspers, dissectors, scissors, clamps, or the like. The distal end of the elongated cylindrical portion 124 is attached by suitable clamping means (not shown) to the tool holding platform of the device of the present invention. Thus, the tool head 126 can be positioned by movement of the tool holding platform. The instrument is described in more detail in U.S. Pat. No. 5,417,203, which is hereby incorporated by reference.

The invention has been described in detail with reference to preferred embodiments thereof. However, it will be appreciated that, upon consideration of the present specification and drawings, those skilled in the art may make modifications and improvements within the spirit and scope of this invention as defined by the claims.

I claim:

1. A surgical tool holding and positioning device capable of providing linear motion along a radius centered remote from an operator, said device comprising:
   an elongated proximal first tubular member having a longitudinal axis, a proximal end and a distal end:
   a distal second tubular member attached to the first tubular member for azimuthal rotation about a fixed point adjacent the distal end of said first tubular member to position the second tubular member to form an angle with respect to the longitudinal axis of the first tubular member;
   a first rod extending from the proximal end and connected to the second tubular member for controlling an azimuthal angular position of the second tubular member with respect to the longitudinal axis of the first tubular member; and
   a second rod extending from the proximal end through the first and second tubular members for supporting and linearly moving a surgical tool alone a radius oriented in any one of a plurality of directions extending from said fixed point.

2. A surgical tool holding and positioning device in accord with claim 1, wherein the second rod has a distal end and further comprising a tool holding member attached at the distal end of the second rod.

3. A surgical tool holding and positioning device in accord with claim 2, further comprising a surgical tool attached to the tool holding member, the surgical tool being operated by tool control means extending through the first and second tubular members for manipulation of the surgical tool from the proximal end of the elongated first tubular member.

4. A surgical tool holding and positioning device in accord with claim 1, further comprising a distal rod that is attached to the second tubular member at one end and to the first rod at the other end, the distal rod pivoting near the distal end of the elongated first tubular member for angular positioning of the second tubular member with respect to the longitudinal axis of the elongated first tubular member.

5. A surgical tool holding and positioning device in accord with claim 4, wherein the distal rod has an L-shape.

6. A surgical tool holding and positioning device in accord with claim 5, wherein the distal rod has a long arm and a short arm at an angle to the long arm, the angle being from about 90° to about 135°.

7. A surgical tool holding and positioning device in accord with claim 4, wherein the distal rod is an integral part of the second tubular member.

8. A surgical tool holding and positioning device in accord with claim 1, wherein the second tubular member is positioned relative to the longitudinal axis of the elongated first tubular member at an azimuthal angle from about 0° to about 150°.

9. A surgical tool holding and positioning device in accord with claim 1, wherein the azimuthal angular position is controlled by a micrometer device attached to the first rod.

10. A surgical tool holding and positioning device in accord with claim 1, wherein the azimuthal angular position is controlled by a rack and pinion device attached to the first rod.

11. A surgical tool holding and positioning device in accord with claim 1, wherein the azimuthal angular position is fixed by a locking device attached to the first rod.

12. A surgical tool holding and positioning device in accord with claim 1, further comprising at the distal end thereof a surgical tool selected from the group consisting of a laser, an ultrasonic transducer, a bipolar cautery device, a monopolar cautery device, an irrigator, an aspirator, an operating microscope and a flexible endoscope for visualization and illumination.

13. A surgical tool holding and positioning device comprising:

an elongated first tubular member having a longitudinal axis, a proximal end and a distal end:

a second tubular member attached to the first tubular member for rotation about a fixed point adjacent the distal end thereof to position the second tubular member to form an angle with respect to the longitudinal axis of the first tubular member;

a first rod extending from the proximal end and connected to the second tubular member for controlling its angular position with respect to the longitudinal axis of the first tubular member; and a second rod extending from the proximal end through the first and second tubular members;

wherein the second rod is linearly movable within the first and second tubular members to vary the position of the distal end of the second rod.

14. A method for using a tool holding and positioning device, said method comprising:

providing a tool holding and positioning device comprising an elongated first tubular member having a longitudinal axis, a proximal end and a distal end; a second tubular member attached to the first tubular member for azimuthal rotation about a fixed point adjacent the distal end thereof to position the second tubular member to form an azimuthal angle with respect to the longitudinal axis of the first tubular member; a first rod extending from the proximal end and connected to the second tubular member for controlling its azimuthal angular position with respect to the longitudinal axis of the first tubular member; and a second rod extending from the proximal end through the first and second tubular members;

inserting the tool holding and positioning device through an aperture into a body so that the distal end of the elongated first tubular member is located in the center of a volume of interest;

fixing the tool holding and positioning device relative to the aperture so that the proximal end extends out from the aperture;

adjusting the first rod to set an azimuthal angular position of the second tubular member with respect to the longitudinal axis of the elongated first tubular member; and extending the second rod through the first and second tubular members to position, independent from said adjusting step, a tool radially with respect to said fixed point for operation within the volume of interest.

15. A method for using a tool holding and positioning device in accord with claim 14, further comprising rotating the elongated first tubular member about its longitudinal axis to reach all points in a cylindrical portion of the region.

16. A method for using a tool holding and positioning device in accord with claim 14, further comprising changing the angular position in the range of from about 0° to about 150° to access additional portions of the region.

17. A method for using a tool holding and positioning device in accord with claim 14, further comprising changing the angular position in the range of from about 0° to about 150° and rotating the elongated first tubular member about its longitudinal axis at each angular position to reach access points in a spherical portion of the region.

18. A method according to claim 14, further comprising linearly varying the radial position of the tool along a fixed azimuthal angle.

* * * * *